United States Patent
Shtekel et al.

(10) Patent No.: US 12,232,877 B2
(45) Date of Patent: Feb. 25, 2025

(54) SYSTEM AND METHOD FOR ARRHYTHMIA DIAGNOSIS

(71) Applicant: INDAMED, Holon (IL)

(72) Inventors: Asher Shtekel, Tirat Yehuda (IL); Chanan Schneider, Tirat Yehuda (IL); Yehuda Schnaps, Gimzo (IL); Vadim Manevich, Holon (IL)

(*) Notice: Subject to any disclaimer, the term of this patent is extended or adjusted under 35 U.S.C. 154(b) by 1231 days.

(21) Appl. No.: 17/268,607

(22) PCT Filed: Feb. 14, 2018

(86) PCT No.: PCT/IL2018/050173
§ 371 (c)(1),
(2) Date: Mar. 1, 2021

(87) PCT Pub. No.: WO2018/150424
PCT Pub. Date: Aug. 23, 2018

(65) Prior Publication Data
US 2021/0353204 A1    Nov. 18, 2021

(30) Foreign Application Priority Data
Feb. 14, 2017 (IL) .......................... 250610

(51) Int. Cl.
*A61B 5/35* (2021.01)
*A61B 5/273* (2021.01)
(Continued)

(52) U.S. Cl.
CPC .............. *A61B 5/35* (2021.01); *A61B 5/273* (2021.01); *A61B 5/282* (2021.01); *A61B 5/364* (2021.01)

(58) Field of Classification Search
CPC ......... A61B 5/271; A61B 5/273; A61B 5/282; A61B 5/35; A61B 5/361; A61B 5/363; A61B 5/364; A61B 5/7246
See application file for complete search history.

(56) References Cited

U.S. PATENT DOCUMENTS 5,311,873 A    5/1994 Savard
5,595,183 A    1/1997 Swanson
(Continued)

OTHER PUBLICATIONS

Chang Yao-Ting et al: "Ablation of ventricular arrhythmia originating at the papillary muscle using an automatic pacemapping module", Heart Rhythm, Elsevier, US, vol. 13, No. 7, Jun. 18, 2016 (Jun. 18, 2016), pp. 1431-1440, XP029617330, ISSN: 1547-5271, 001: 10.1016/J.HRTHM. Mar. 17, 2016.

*Primary Examiner* — Amanda K Hulbert
(74) *Attorney, Agent, or Firm* — AlphaPatent Associates Ltd.; Daniel J. Swirsky

(57) ABSTRACT

A method for diagnosing arrhythmia focus in the heart of a patient comprising: affixing electrodes to a patient; providing a wearable monitor and connecting the electrodes to a wearable monitor; monitoring the patient by the wearable monitor for a monitoring period to produce a wearable ECG waveform; disconnecting the wearable monitor from the electrodes while leaving the electrodes affixed to the patient or marking the positions of these electrodes; providing a waveform analyzer running on a computer; importing the wearable ECG waveform into the waveform analyzer; defining a composite arrhythmia waveform from the wearable ECG waveform; providing an EP lab ECG and connecting the electrode stickers to the EP lab ECG or connecting new stickers to the marked positions; pacing the heart of the patient using a pacing catheter; and comparing the paced ECG waveform provided by the EP lab ECG with the composite arrhythmia waveform to diagnose the arrhythmia focus.

8 Claims, 13 Drawing Sheets

(51) Int. Cl.
    *A61B 5/282*     (2021.01)
    *A61B 5/364*     (2021.01)

(56)             References Cited

U.S. PATENT DOCUMENTS 6,944,495  B2    9/2005   MacAdam
    7,123,954  B2   10/2006   Narayan
    7,245,962  B2    7/2007   Ciaccio
    7,411,509  B2    8/2008   Rosenfeld
    7,783,352  B1    8/2010   Ryu
    9,386,935  B2    7/2016   Kimura
 2001/0056245  A1   12/2001   Mlynash
 2004/0059237  A1    3/2004   Narayan
 2006/0025697  A1    2/2006   Kurzweil
 2008/0109040  A1    5/2008   Belardinelli
 2010/0112081  A1    5/2010   Mishra
 2010/0280841  A1   11/2010   Dong
 2014/0128757  A1    5/2014   Banet
 2016/0166165  A1    6/2016   Govari
 2016/0296171  A1*  10/2016   Drori .................. A61B 5/1072
 2018/0289278  A1   10/2018   Nakazawa

* cited by examiner

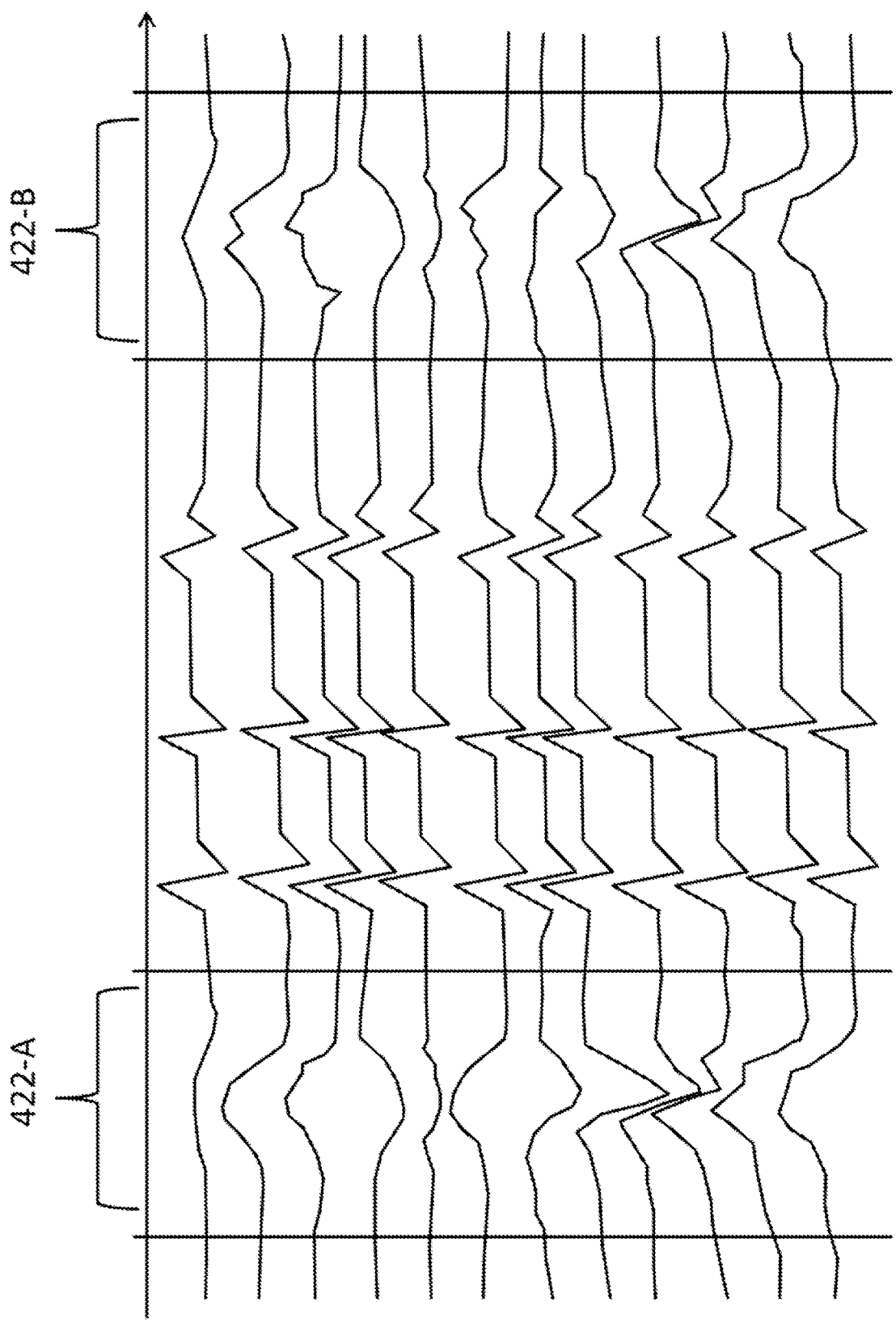

SYSTEM AND METHOD FOR ARRHYTHMIA DIAGNOSIS

CROSS-REFERENCE TO RELATED APPLICATIONS

This application is a U.S. National Phase Application under 35 U.S.C. 371 of International Application No. PCT/IL2018/050173, which has an international filing date of 14 Feb. 2018, and which claims the benefit of priority from Israel Patent Application No. IL 250610, filed 14 Feb. 2017, the disclosures of which are incorporated herein by reference in their entirety.

FIELD OF THE INVENTION

The present invention is of a system and method for arrhythmia diagnosis and in particular, such a system and method that significantly improves the arrhythmia focus diagnostic process.

BACKGROUND OF THE INVENTION

Pace mapping is frequently used in clinical practice as a means for diagnosing ventricular arrhythmia focus. The method of diagnosis generally includes the following steps: A patient is diagnosed with arrhythmia from an electrocardiogram (ECG) recorded using a recorder in a clinic, or from a wearable heart monitor/recorder worn for a specified period of time.

The patient is then invited to an electrophysiology lab (EP lab) or clinic where they are connected to a lab ECG. The output ECG is monitored till the previously diagnosed arrhythmia takes place again. If it does, then the ECG waveform observed during arrhythmia is used as a template and is mapped against an ECG waveform recorded while performing pace mapping using a pacer catheter to pace different areas of the heart. Pacer catheter may also be referred to as a roving or EP catheter. Current computerized comparison systems include, for example, the PaSo module in the CARTO mapping system manufactured by Biosense Webster® or other similar systems from different manufacturers. The pace mapping continues until the focus is diagnosed when the paced and template waveforms overlap to a high percentage (90-95%).

If the diagnosed arrhythmia does not occur spontaneously, attempts will be made to induce the arrhythmia using drugs such as catecholamine and/or cardiac stimulation. However, even with these measures, in as many as 20% of cases the diagnosed arrhythmia will not occur in the EP lab. There are several possible reasons why arrhythmia does not occur in the EP lab including: the intermittent nature of the arrhythmia; the limited time available for the procedure per patient; arrhythmia occurrence is only with particular triggers such as exercise, meals, smoking etc.; sedation of the patient during the procedure prevents arrhythmia; and difficulty with recognition of the "dominant" or "clinically relevant" arrhythmia type with small amounts of arrhythmia, multiple waveforms, and "artificial" arrhythmia caused by catheter movement within the heart. When arrhythmia does not occur or cannot be reproducibly induced, the procedure is abandoned.

The procedure as used today is now described in more detail. Reference is made to FIGS. 1A and 1B which are respectively a schematic system diagram and a flow diagram showing a prior art system and method for diagnosis of the arrhythmia focus. As in FIG. 1B, in stage 1 electrode stickers 102 are affixed to a patient. These are then connected to electrode cables 103 of a wearable recorder 104. Electrode cables may also be referred to as leads or wires. The wearable recorder 104 may also be referred to as a Holter, Holter monitor, Loop recorder, Event recorder or ambulatory electrocardiography device. Wearable recorders 104 currently used in the art typically have one to three cables 103.

Additionally, in stage 1, the recorder 104 records heart activity as an electrocardiograph (ECG) waveform 106 for an extended period of time typically varying between 24 hours and 4 weeks. Recorder 104 comprises filters 107 for filtering out noise and enhancing the output WF 106. The recording may either be constant or may be intermittent. Intermittent recording is generally patient-initiated wherein the patient usually presses a button or otherwise interacts with the recorder to indicate that a cardiac event is occurring and to start a recording period.

While wearing the recorder 104, the patient is outside the electrophysiology (EP) lab and goes about daily activities. EP Lab as used herein may refer to any clinic or hospital facilities where invasive arrhythmia diagnosis and therapy is performed. The output of recorder is herein referred to as wearable ECG waveform (WF) 106. ECG WF 106 is stored in recorder 104 on a recording medium, typically flash memory.

Once sufficient data has been gathered or after a defined period of analysis, electrodes 103 and electrode stickers 102 are removed from the patient and the recorder 104 is returned to the clinic for analysis. The ECG waveform 106 is then analyzed, optionally using ECG analysis software to detect arrhythmia patterns. In stage 2, following such analysis, the identified arrhythmia patterns are reviewed and a clinical diagnosis of arrhythmia is made. In some cases it will be determined that the arrhythmia requires further invasive diagnosis and potentially ablation in the EP lab.

Having made a clinical diagnosis of arrhythmia requiring invasive diagnosis, the patient will now return to the EP lab for diagnosis of the arrhythmia focus within the heart, with an intention to perform curative therapy by ablation (cauterization). In stage 3, electrode stickers 110 are affixed to the patient and electrode cables 111 of EP lab recorder 112 are attached to stickers 110. EP lab recorders 112 as used in the art typically use twelve stickers 110 and ten cables 111. EP lab recorder 112 produces EP lab electrocardiogram (ECG) waveform 114. Lab recorder 112 comprises filters 113 for filtering out noise and enhancing the output WF 114. Filters 113 are different to filters 107 and are configured differently. ECG waveform 114 is provided to pace mapping system 120. System 120 comprises a visual display (not shown) for viewing the lab ECG waveform 114 of recorder 112.

In stage 4, ECG waveform 114 is analyzed within system 120 for detection of an arrhythmia event as observed in the analysis of wearable ECG WF 106. As above, this event may not occur spontaneously and, at stage 5, if arrhythmia is not detected, attempts will be made at stage 6 to induce arrhythmia. These attempts will continue and stages 4, 5, and 6 will be repeated until arrhythmia as previously detected is observed. If the arrhythmia is not observed after significant efforts or if no further time is available, as in stage 6A the procedure will be abandoned.

In stage 7, if arrhythmia as previously detected in ECG WF 106 is observed in EP lab ECG waveform 114 on mapping system 120, the observed arrhythmia waveform is defined as a template waveform 122 for mapping. In stage 8, pace mapping is now performed by probing areas of the heart with pacer catheter 130. ECG waveform 114 is now used by system 120 to provide paced waveform 124 which changes as pacer catheter 130 is moved to different positions. Paced waveform 124 is compared to arrhythmia template waveform 122 until the arrhythmia focus is determined at stage 9. Curative therapy by ablation may then be performed.

As shown, the current method requires repeated arrhythmia diagnosis (first of the wearable WF 106 and then again with lab WF 114), is unduly complicated and unpredictable, particularly in stages 3-6, and more importantly, may result in a failure to diagnose the arrhythmia focus (stage 6A) resulting in medical danger to the patient as well as frustration of clinical staff. Current methods and systems also do not enable use of the wearable waveform 106 in the pace mapping system 120 as it is based on fewer leads, is not accurate enough, and relies on different filters. Further there is no method for importing waveform 106 into system 120.

Thus, there is an urgent need for a solution that streamlines the arrhythmia focus diagnostic process and that significantly increases the probability of diagnosing the arrhythmia focus.

SUMMARY OF THE INVENTION

The present invention overcomes the deficiencies of the background art by providing a system and method for improving the arrhythmia focus diagnostic process. The present invention aims to prevent the situation as described above with the prior art where arrhythmia that is diagnosed outside of the EP cannot be replicated inside the EP lab.

This is achieved by using the ECG waveform from a specially adapted wearable monitor and providing an analyzer computer or software module that can import this waveform, for use in defining an arrhythmia template for the patient based on an arrhythmia event or events that have occurred outside the EP lab while wearing the wearable monitor.

Further, once the arrhythmia template is defined it can be imported into the pace mapping system. Either the analyzer is adapted to export the template in a format that the pace mapping system can utilize (when the analyzer is a separate computer), or the analyzer is a software module that is part of the pace mapping system and this software module can provide the template to the mapping module of the pace mapping system.

To ensure that the ECG waveform from the wearable monitor and the waveform from the EP lab ECG monitor are compatible, the electrode sticker position must be the same. Therefore, either the electrode stickers are left in positon affixed to the patient or their position is marked so that stickers in the EP lab can be affixed to the same positions. Additionally, the same filters and settings used in producing the wearable ECG waveform must be used to produce the EP lab ECG waveform.

Once the template is imported, pace mapping can be performed using a catheter to probe points in the heart of the patient until a match with the template is found (based on the output of the output of the EP lab ECG monitor) and the arrhythmia focus is thus determined. Curative ablation or other therapy may then be performed.

Therefore by providing a system and method for importing the ECG with the arrhythmia detected outside the EP lab, the situation as described in the introduction, where the arrhythmia cannot be duplicated in the EP lab, is remedied. Further, the process is simplified as shown further below.

According to some embodiments of the present invention, a method for diagnosing arrhythmia focus in the heart of a patient comprises: affixing a plurality of electrode stickers to a patient; providing a wearable monitor and connecting the stickers to a wearable monitor; monitoring the patient by the wearable monitor for a monitoring period to produce a wearable ECG waveform; disconnecting the wearable monitor from the stickers while leaving the stickers affixed to the patient; providing a waveform analyzer running on a computer; defining an arrhythmia template waveform by the waveform analyzer from the wearable ECG waveform; providing an EP lab ECG recorder and connecting the stickers to the EP lab ECG recorder; pacing the heart of the patient using a pacing electrode; and comparing the paced ECG waveform provided by the EP lab ECG recorder with the template waveform to diagnose the arrhythmia focus.

Preferably the plurality of electrode stickers comprises up to ten stickers. Preferably the wearable monitor comprises a plurality of electrode cables and the cables are used for the connecting the stickers to the wearable monitor. Preferably the plurality of electrode cables comprises up to 12 electrode cables for recording up to a 12 channel ECG. Preferably the wearable ECG waveform is stored on the wearable monitor. Optionally the wearable ECG waveform is stored in a format selected from the group consisting of SCP-ECG, DICOM-ECG, and HL7 aECG.

Preferably the ECG waveform comprises up to twelve channels. Preferably the wearable monitor filters the signal received from the electrode stickers using filters. Optionally, the filters are selected from the group consisting of low pass, high pass, band pass, notch filters and a combination of the above and the filters have settings that can be configured. Optionally the monitoring period is at least 72 hours.

Preferably the method further comprises importing the wearable ECG waveform into the analyzer and wherein the importing comprises connection of one of the recorder or recorder media to the analyzer by at least one of wireless or wired connection. Preferably the analyzer is adapted to process the wearable ECG waveform. Preferably, the recorder stores the wearable ECG WF in a storage format that can be processed by the analyzer. Optionally the analyzer comprises a translation module and translates the wearable ECG waveform into a format that it can process using the translation module. Preferably the comparing of the paced ECG waveform with the template waveform is performed by a pace mapping system running on a computer. Optionally the pace mapping system and the analyzer run on the same computer. Preferably the method further comprises importing the template waveform into the pace mapping system and wherein the method of the importing the template waveform is selected from the group consisting of: adapting the template waveform to a file format that can be used by the pace mapping system and importing the file into the pace mapping system; connecting the analyzer to the pace mapping system via the ECG input port of the pace mapping system and mimicking by the analyzer the signal that an ECG device would provide to the port; adapting the template waveform to an image file format that can be used by the pace mapping system and importing the file into the pace mapping system; and a combination of the above.

Preferably the template waveform is stored in the internal storage of the pace mapping system. preferably the EP lab recorder comprises a plurality of electrode cables and the cables are used for the connecting the stickers to the EP lab recorder. Preferably the EP lab recorder comprises EP lab recorder filters and wherein the EP lab recorder filters are the same as the filters and are configured with the same filter settings. Preferably the EP lab recorder records up to 12 channels. Preferably the defining an arrhythmia template waveform by the waveform analyzer requires interaction with the analyzer by an operator.

According to some embodiments of the present invention, a system for diagnosing arrhythmia focus in the heart of a patient comprises: electrode stickers for affixing to a patient; a wearable ECG monitor with cables for connecting to the stickers and adapted to record a wearable ECG waveform; a waveform analyzer running on a computer adapted for defining an arrhythmia template waveform from the wearable ECG waveform; an EP lab ECG recorder with cables for connecting to the stickers and adapted to record a pacing ECG waveform; and a pace mapping system running on a computer comprising a pacing electrode for pacing the heart of the patient; wherein the pacing ECG waveform is compared with the template waveform to diagnose the arrhythmia focus.

Preferably the wearable monitor comprises recording media and wearable ECG waveform is stored on the recording media. Optionally the wearable ECG waveform is stored in a format selected from the group consisting of SCP-ECG, DICOM-ECG, and HL7 aECG. Preferably the wearable ECG waveform comprises up to twelve channels. Preferably the wearable monitor comprises filters for filtering the signal received from the electrode stickers. Optionally the filters are selected from the group consisting of low pass, high pass, band pass, notch filters and a combination of the above and have setting that can be configured.

Preferably the analyzer comprises at least one of a wireless or wired connection for connecting the wearable recorder or recorder media to the analyzer. Optionally the analyzer comprises a translation module for translating the wearable ECG waveform into a format that it can process. Optionally the pace mapping system and the analyzer run on the same computer. Preferably the EP lab recorder comprises EP lab recorder filters and wherein the EP lab recorder filters are the same as the filters and are configured with the same filter settings. Preferably the EP lab recorder records up to 12 channels.

According to some further embodiments of the present invention, a method for diagnosing arrhythmia focus in the heart of a patient comprises: affixing a plurality of electrode stickers to a patient; providing a wearable monitor and connecting the stickers to a wearable monitor; monitoring the patient by the wearable monitor for a monitoring period to produce a wearable ECG waveform; disconnecting the wearable monitor from the stickers and marking the positions of before removing the stickers from the patient; providing a waveform analyzer running on a computer; importing the wearable ECG waveform into the waveform analyzer; defining an arrhythmia template waveform from the wearable ECG waveform; affixing a plurality of electrode stickers to a patient in the positions previously marked on the patient; providing an EP lab ECG and connecting the stickers to the EP lab ECG; pacing the heart of the patient using a pacing electrode; and comparing the paced ECG waveform provided by the EP lab ECG with the template waveform to diagnose the arrhythmia focus.

According to further embodiments of the present invention, a system for diagnosing arrhythmia focus in the heart of a patient comprises: affixing a plurality of electrode stickers to a patient; providing a wearable monitor and connecting the stickers to a wearable monitor; monitoring the patient by the wearable monitor for a monitoring period to produce a wearable ECG waveform; providing a waveform analyzer running on a computer; importing the wearable ECG waveform into the waveform analyzer; defining an arrhythmia template waveform from the wearable ECG waveform; pacing the heart of the patient using a pacing electrode; and comparing the paced ECG waveform provided by the wearable monitor with the template waveform to diagnose the arrhythmia focus.

According to further embodiments of the present invention a method for diagnosing arrhythmia focus in the heart of a patient comprises: affixing a plurality of electrode stickers to a patient; providing a wearable monitor and connecting said stickers to a wearable monitor; monitoring the patient by said wearable monitor for a monitoring period to produce a wearable ECG waveform; disconnecting said wearable monitor from said stickers while performing at least one of: leaving said stickers affixed to the patient; or marking the positions of said stickers before removing said stickers; defining a composite arrhythmia waveform from said wearable ECG waveform; providing an EP lab ECG recorder and performing at least one of: connecting said stickers to said EP lab ECG recorder; or connecting a second set of stickers to said EP lab ECG recorder wherein said second set of stickers are positioned on the marked positions; pacing the heart of the patient using a pacing electrode; and comparing the paced ECG waveform provided by said EP lab ECG recorder with said composite arrhythmia waveform to diagnose the arrhythmia focus.

Preferably the method further comprises providing a waveform analyzer and wherein said composite arrhythmia waveform is defined using said analyzer. Preferably said composite arrhythmia waveform comprises at least one arrhythmia waveform detected in wearable ECG waveform. Preferably detecting said at least one arrhythmia waveform comprises at least one of: said analyzer automatically detecting said at least one arrhythmia WF; an operator of said analyzer detecting said at least one arrhythmia WF; or a combination of the above.

Preferably said plurality of electrode stickers comprises up to ten stickers. Preferably said plurality of electrode stickers comprise a die for marking the positons of said stickers on a patient. Preferably the wearable monitor comprises a plurality of electrode cables and said cables are used for said connecting said stickers to said wearable monitor. Preferably said plurality of electrode cables comprises 12 electrode cables. Preferably said wearable ECG waveform is stored on said wearable monitor. Preferably said wearable ECG waveform is stored in a format selected from the group consisting of SCP-ECG, DICOM-ECG, and HL7 aECG. Preferably said wearable ECG waveform comprises up to twelve channels. Preferably said wearable monitor filters the signal received from said electrode stickers using filters.

Preferably said filters are selected from the group consisting of low pass, high pass, band pass, notch filters and a combination of the above. Preferably the monitoring period is at least 72 hours. Preferably said importing said wearable ECG waveform into said analyzer comprises connection of one of said recorder or recorder media to said analyzer by at least one of wireless or wired connection. Preferably said analyzer is adapted to process said wearable ECG waveform. Preferably said recorder stores said wearable ECG WF in a storage format that can be processed by said analyzer. Preferably said analyzer comprises a translation module and translates said wearable ECG waveform into a format that it can process using said translation module.

Preferably said comparing of said paced ECG waveform with said composite waveform is performed by a pace mapping system running on a computer. Preferably said pace mapping system and said analyzer run on the same computer. Preferably the method further comprises: importing said composite waveform into said pace mapping system. Preferably said composite waveform is transferred to a storage device and said storage device is connected to said pace mapping system for importing said composite waveform from said storage device into said pace mapping system. Preferably the method of said importing said composite waveform is selected from the group consisting of: adapting said composite waveform to a file format that can be used by said pace mapping system and importing said file into said pace mapping system; connecting said analyzer to said pace mapping system via the ECG input port of said pace mapping system and mimicking by said analyzer the signal that an ECG device would provide to said port; adapting said composite waveform to an image file format that can be used by said pace mapping system and importing said file into said pace mapping system; and a combination of the above.

Preferably said composite waveform is stored in the internal storage of said pace mapping system. Preferably the EP lab recorder comprises a plurality of electrode cables and said cables are used for said connecting said stickers to said EP lab recorder. Preferably said EP lab recorder comprises EP lab recorder filters and wherein said EP lab recorder filters are the same as said filters and are configured with the same filter settings. Preferably said EP lab recorder records up to 12 channels. Preferably said defining a composite arrhythmia waveform by said waveform analyzer requires interaction with said analyzer by an operator.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Although the present invention is described with regard to a "computing device", a "computer", or "device", or "mobile device" on a "computer network" or simply "network", it should be noted that optionally any device featuring a data processor and the ability to execute one or more instructions may be described as a computer or one of the interchangeable terms listed above, including but not limited to any type of personal computer (PC), a server, a cellular telephone, an IP telephone, a smartphone, or a PDA (personal digital assistant). Any two or more of such devices in communication with each other may optionally comprise a "network".

BRIEF DESCRIPTION OF THE DRAWINGS

The invention will now be described in connection with certain preferred embodiments with reference to the following illustrative figures so that it may be more fully understood. With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 4D-4E are exemplary ECG waveforms according to some embodiments of the present invention.

DETAILED DESCRIPTION OF PREFERRED EMBODIMENTS

In the detailed description, numerous specific details are set forth in order to provide a thorough understanding of the invention. However, it will be understood by those skilled in the art that these are specific embodiments and that the present invention may be practiced also in different ways that embody the characterizing features of the invention as described and claimed herein.

Figure 1A:
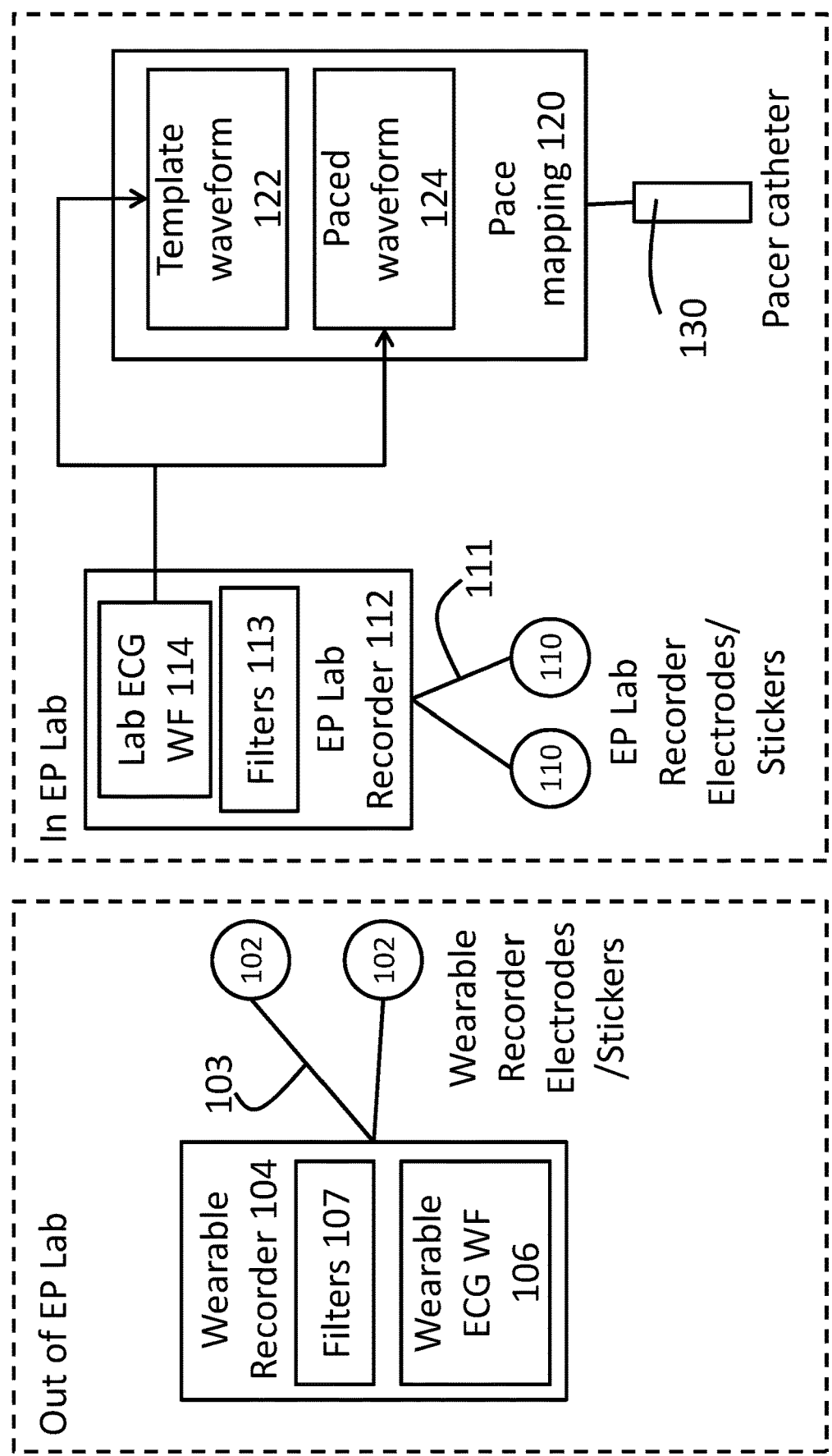
FIGS. 1A and 1B are respectively a schematic system diagram and a flow diagram showing a prior art system and method for diagnosis of the arrhythmia focus.
Figure 1B:
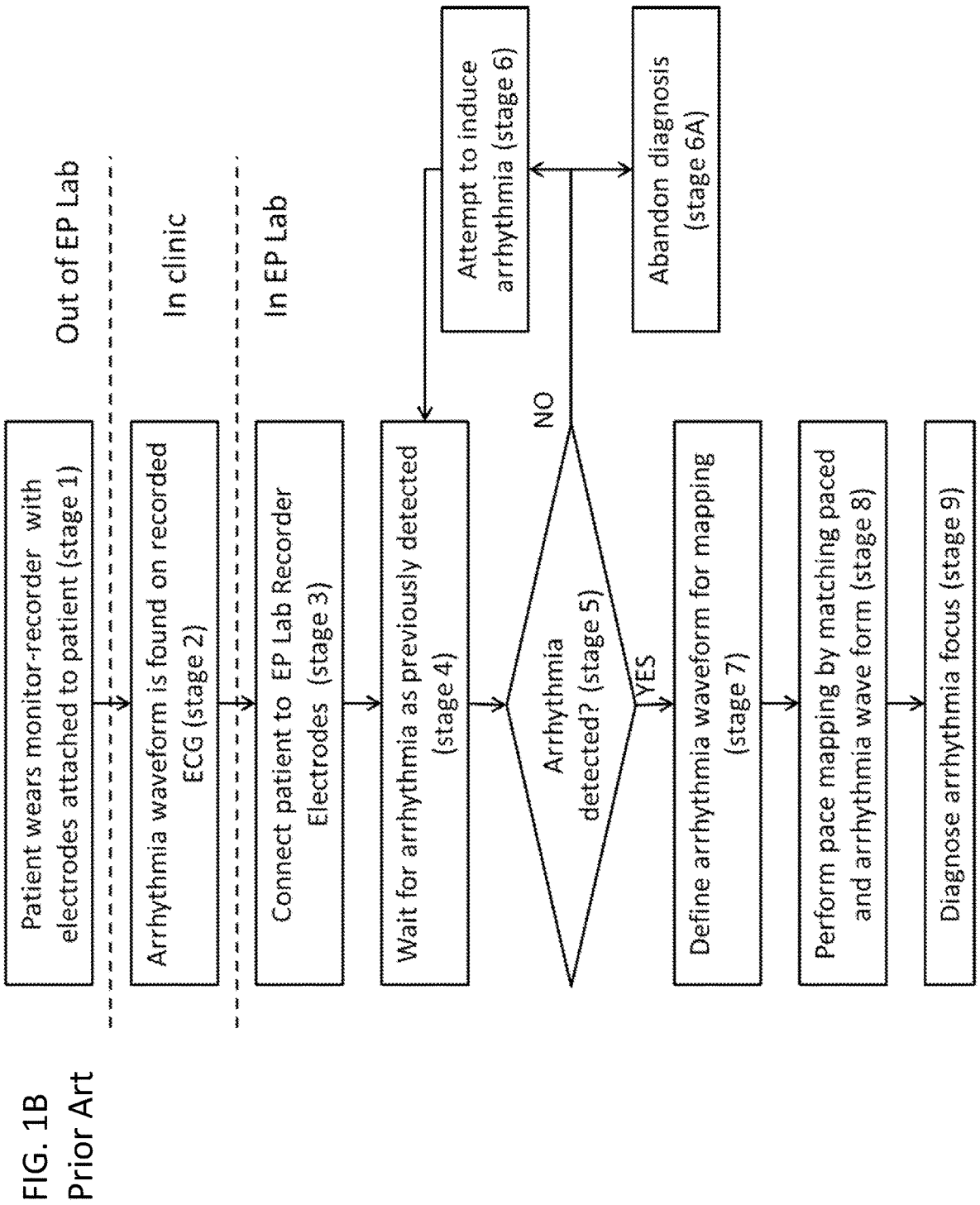
Figure 2A:
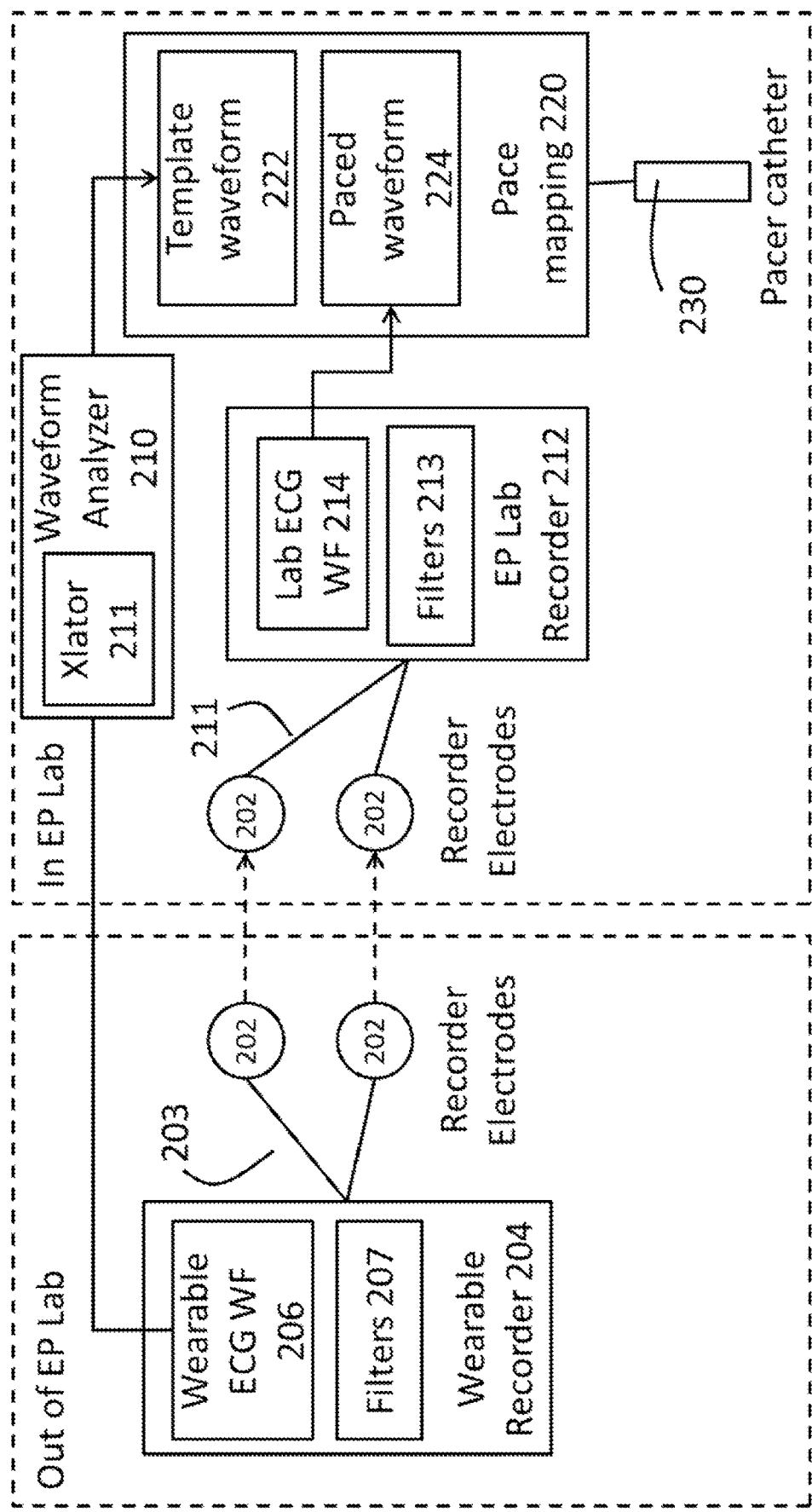
FIGS. 2A-2C are schematic system diagrams and a flow diagram showing system and method for diagnosis of arrhythmia focus according to some embodiments of the present invention.
Figure 2B:
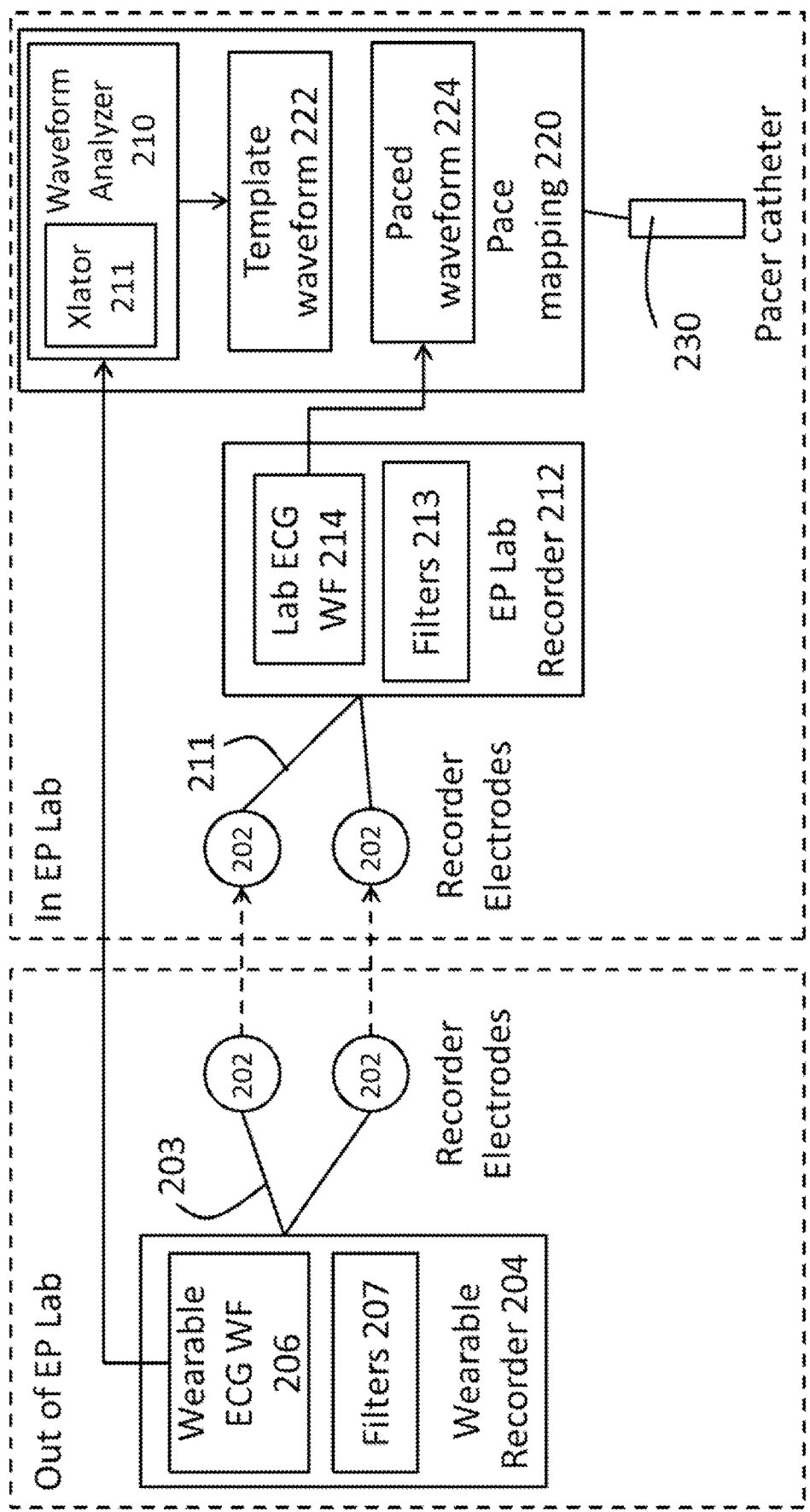
Figure 2C:
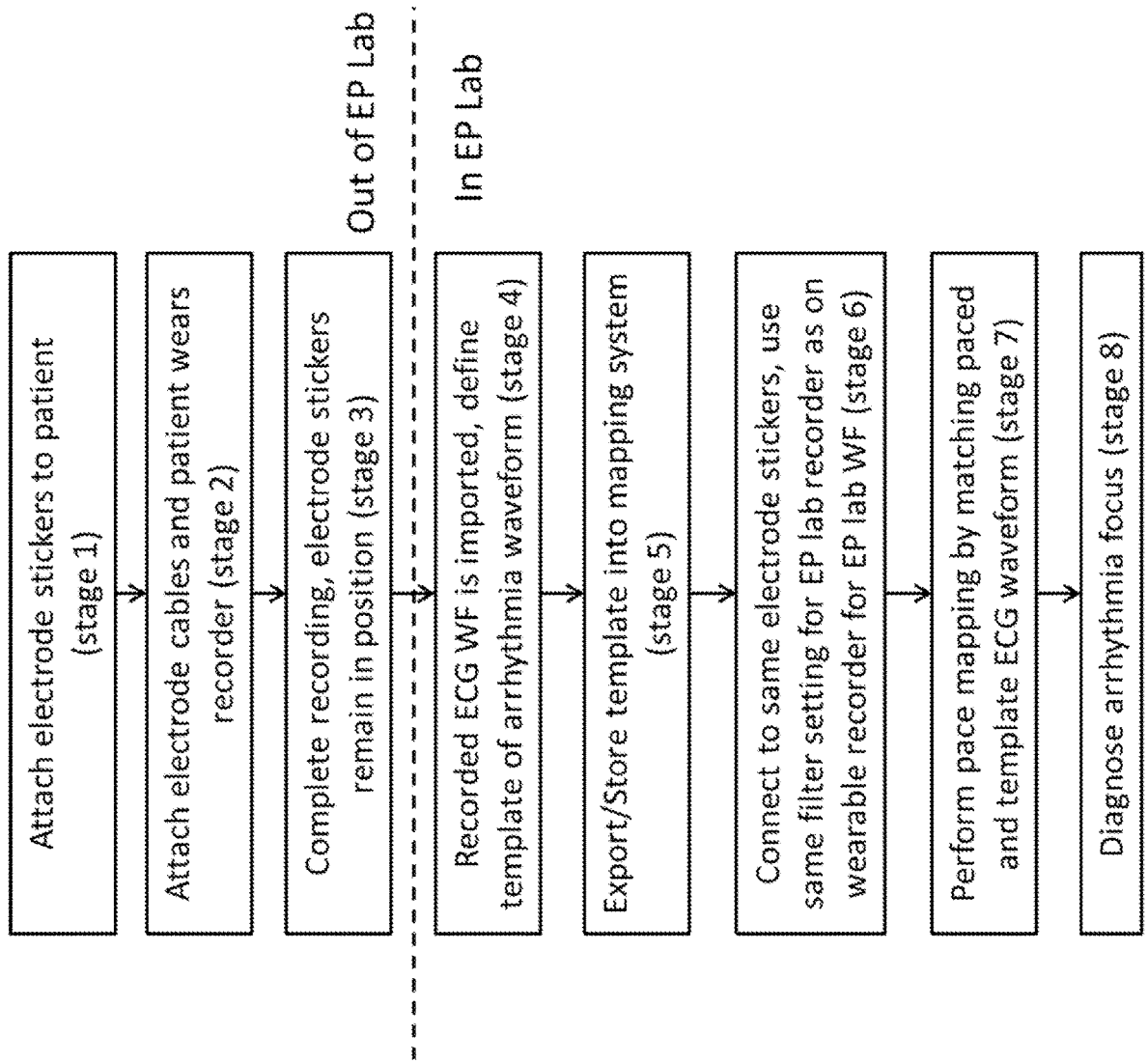

The present invention will be more fully understood from the following detailed description of the preferred embodiments thereof, taken together with the drawings. Reference is now made to FIGS. 2A-2C, which are schematic system diagrams and a flow diagram showing a system and method for diagnosis of arrhythmia focus according to some embodiments of the present invention.

As in FIG. 2C, in stage 1 electrode stickers 202 are affixed to a patient. Most preferably ten stickers 202 are affixed to the patient. The sticker placement is as known in the art for 12-lead ECG recording. In stage 2, twelve electrode cables 203 are connected to the stickers 202. Electrode cables 203 are connected to a wearable recorder 204 worn by the patient. Wearable recorder 204 is adapted for 12-lead ECG recording. Recorder 204 then records heart activity as an ECG waveform 206 for an extended period of time typically varying between 24 hours and 72 hours. During this time the patient is outside the EP lab and goes about daily activities.

The output of recorder 204 is herein referred to as wearable ECG waveform (WF) 206. ECG WF 206 preferably comprises 12 channels. Optionally, any number of channels may be recorded that provides sufficient data for arrhythmia diagnosis as described herein. ECG WF 206 is stored in recorder 204 on a recording medium. A non-limiting example of a recording medium is flash memory, but other forms of storage may be used. Non-limiting examples of ECG storage formats include SCP-ECG, DICOM-ECG, and HL7 aECG, but other formats may be used. Recorder 204 uses filters 207 to enhance the signal received from electrode stickers 202 and cables 203. Non limiting examples of filters 207 include low pass, high pass, band pass, and notch filters or a combination of these. Filters 207 are configurable and comprise settings that can be duplicated in the same filters used in other ECG recorders. In stage 3, once sufficient ECG waveform data has been gathered or after completion of the monitoring period, electrode stickers 202 remain affixed to the patient and electrode cables 203 are disconnected from stickers 202 and the recorder 204 is returned to the EP lab for analysis. Analysis may be optionally be performed in a clinic or lab associated with EP lab. Alternatively, stickers 202 are removed and their exact positioning on the patient is marked, such as with a non-limiting example of a marker pen. Alternatively and preferably stickers 202 are provided with a dye or ink which marks the skin of the patient such that a mark indicating the position of sticker 202 is left on the patient from the dye after sticker 202 is removed.

In stage 4, ECG waveform 206 is imported from recorder 204 into waveform analyzer 210. The importing of ECG WF 206 is performed by wired or wireless connection of recorder 204 to analyzer 210 followed by interaction by an operator with analyzer 210 to initiate the importing. Alternatively the storage media is extracted from recorder 204 and inserted into a storage media reader connected wired or wirelessly to analyzer 210. Alternatively, the importing comprises exporting from the recorder 204 by interaction with the recorder 204. Analyzer 210 is adapted to process the ECG WF 206 in the ECG storage format used by recorder 204. Alternatively, recorder 204 stores ECG WF 206 in an ECG storage format that can be processed by analyzer 210. Alternatively, analyzer 210 translates the ECG WF 206 ECG format provided by recorder 204 into a format that it can process using a translation module 211 (shown in FIG. 2A as xlator 211). Processing includes manipulation and analysis as described below.

In the embodiment of FIG. 2A, waveform analyzer 210 runs on a standalone computer. Alternatively, in the embodiment of FIG. 2B, analyzer 210 is a software module running on the same computational hardware as pace mapping system 220 described below.

Analyzer 210 preferably comprises a screen (not shown) and interaction means such as a keyboard and mouse (not shown) for viewing and manipulating wearable ECG waveform 206.

Figure 3A:
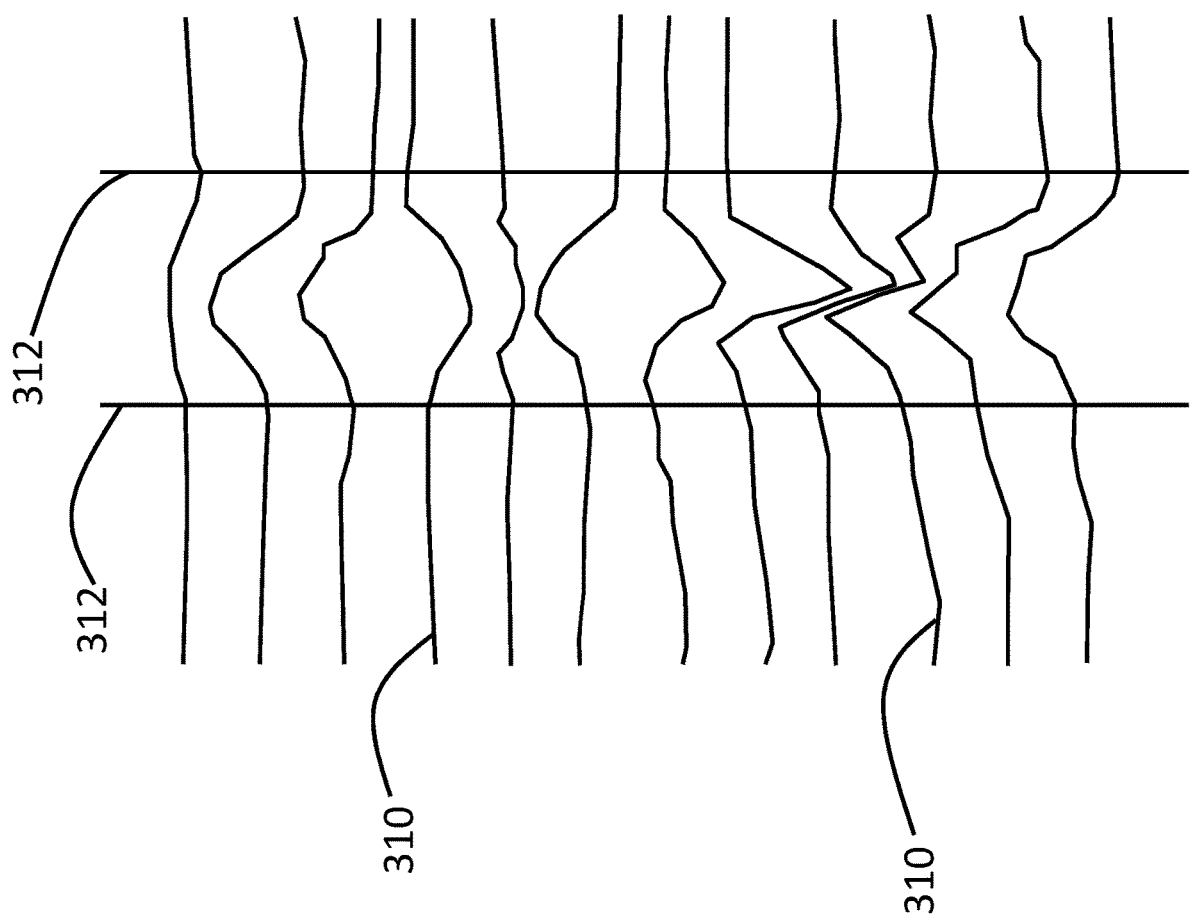
FIGS. 3A-3C are exemplary ECG waveforms according to some embodiments of the present invention.

ECG waveform 206 is then analyzed optionally using ECG analysis software to detect arrhythmia waveform patterns. The operator/practitioner now interacts with analyzer 210 to define at least one of the identified waveforms as an arrhythmia template waveform 222 for later use during pace mapping of arrhythmia focus. FIG. 3A provides an illustration of an identified arrhythmia template waveform ready to be exported from analyzer 210.

In stage 5, for the embodiment of FIG. 2A, the arrhythmia template waveform 222 is exported from analyzer 210 using wired or wireless means into pace mapping system 220. The export format is preferably adapted to suit the mapping system 220 used. Optionally, analyzer 210 connects to system 220 via the ECG input port (not shown) of system 220 and mimics the signal that an ECG device would provide such that system 220 displays the received template waveform 222 which can then be saved in system 220 as the template waveform 222. Alternatively, template waveform 222 may be saved and exported by analyzer 210 as any standard image file type not limited to jpeg, BMP, PNG, or similar for use by system 220.

Alternatively, as in the embodiment of FIG. 2B where analyzer 210 is a software module of system 220, the template 222 is stored in the internal storage of system 220 for use during the pace mapping. Alternatively, the template is stored in a separate file store (not shown).

The patient will now return to the EP lab for diagnosis (mapping) of the arrhythmia focus within the heart. Electrode stickers 202 are still affixed to the patient from stage 1. Alternatively, new stickers 202 are affixed at exactly the previously marked positions. In stage 6 electrode stickers 202 are connected to electrode cables 211 of EP lab recorder 212. EP Lab recorder 212 refers to an ECG recorder preferably for 12 channel recording. EP lab recorder 212 comprises filters 213 which are the same as filters 207 and are configured with the same filter settings that were used by filters 207 on wearable recorder 204 for recording wearable ECG WF 206. Optionally, translation module 211 also comprises a filter adaptor module (not shown) for adjusting the ECG WF 206 to match lab ECG WF 214 based on the filters 213 used in EP lab recorder 212. Optionally, wearable recorder 204 is used as EP lab recorder 212, and electrodes 202 optionally remain connected to recorder 204 or are reconnected in the EP lab.

EP lab recorder 212 produces EP lab ECG waveform 214. ECG waveform 214 is provided to pace mapping system 220. System 220 comprises a visual display (not shown) for viewing the lab ECG waveform 214 of recorder 212. The use of the same sticker positions, number of leads, channels and filters ensures that wearable ECG WF 206 and lab ECG WF 214 are compatible and that template waveform 222 can be used as a basis for comparison with paced waveform 224 as described below.

Figure 3B:
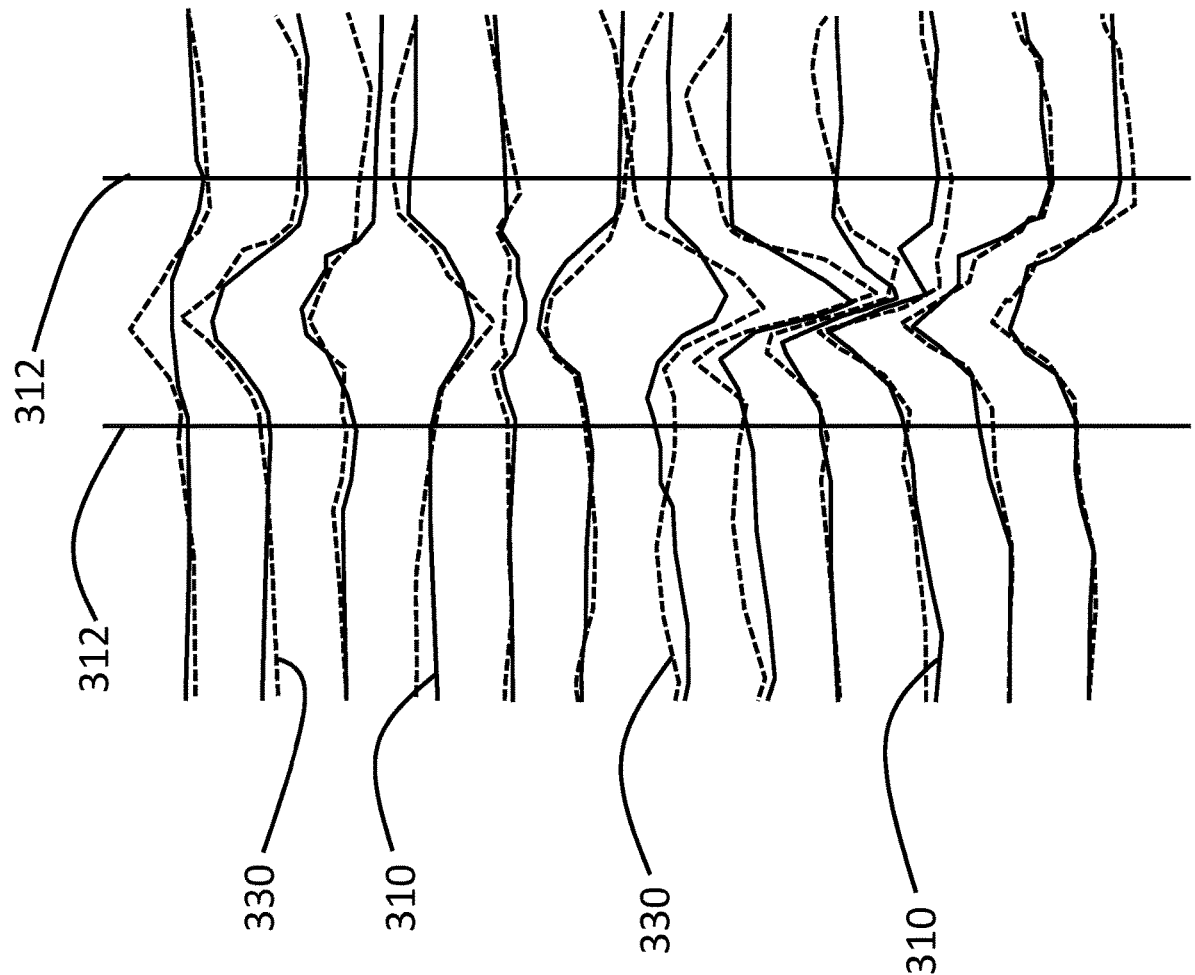
Figure 3C:
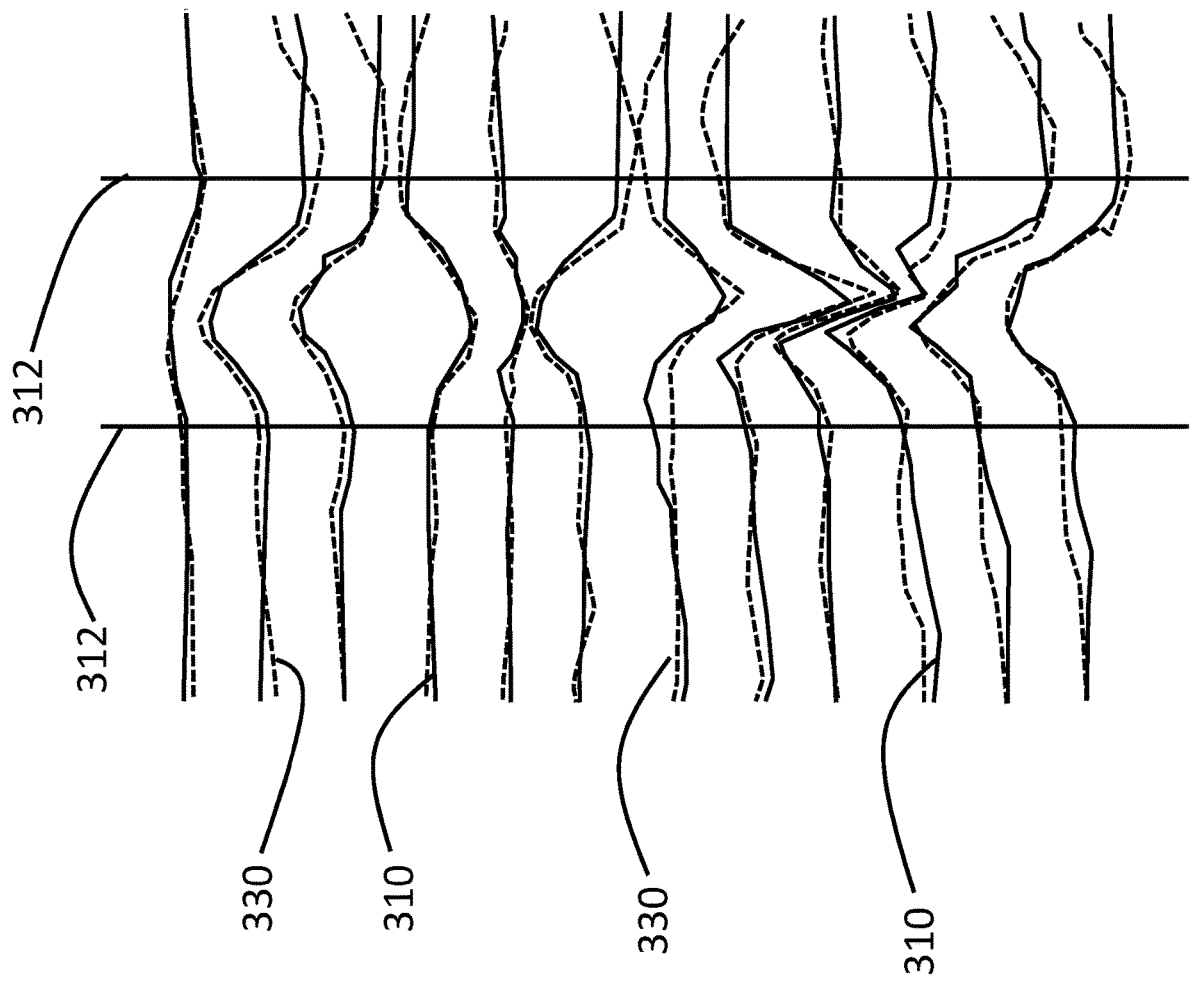

In stage 7, pacing is now performed by probing areas of the heart with pacer catheter 230. ECG waveform 214 is now used by system 220 to provide and display paced waveform 224 which changes as pacer catheter 230 is moved to different positions in the heart. Paced waveform 224 is compared to arrhythmia template waveform 222, defined in stage 4 and exported in stage 5, until the waveforms sufficiently match and arrhythmia focus is diagnosed at stage 8. Preferably, the comparison is performed by system 220 which provides a numeric percentage match indication on a screen (not shown), such that the medical practitioner can determine the arrhythmia focus based on a high percentage match indication, preferably above 95%. Preferably comparison comprises display of the template and paced waveforms overlapped on the screen (not shown) as illustrated in FIGS. 3B and 3C. Following diagnosis, curative therapy by ablation or other means known in the art may then be performed.

Reference is now made to FIGS. 3A-3C which are exemplary ECG waveforms according to some embodiments of the present invention. FIG. 3A shows a twelve lead ECG waveform with 12 channels. As shown, an arrhythmia event is defined by definition lines 312. The arrhythmia event as defined by lines 312 is used as an arrhythmia template waveform such as waveform 222 described above.

FIG. 3B shows visual comparison of the template waveform of FIG. 3A with a paced ECG waveform such as waveform 224 described above. Comparison is performed by superimposing template channels 310 on top of paced waveform channels 330. As in FIG. 3A, the arrhythmia event area is defined by lines 312. In the exemplary comparison of FIG. 3B, the template and paced waveforms do not match to a sufficient percentage since the pacer catheter is not close enough to the arrhythmia focus in the heart.

In the exemplary comparison of FIG. 3C the template and paced waveforms match well to a high percentage since the pacer catheter is close to the arrhythmia focus in the heart and a successful diagnosis of the arrhythmia focus is accomplished.

Figure 4A:
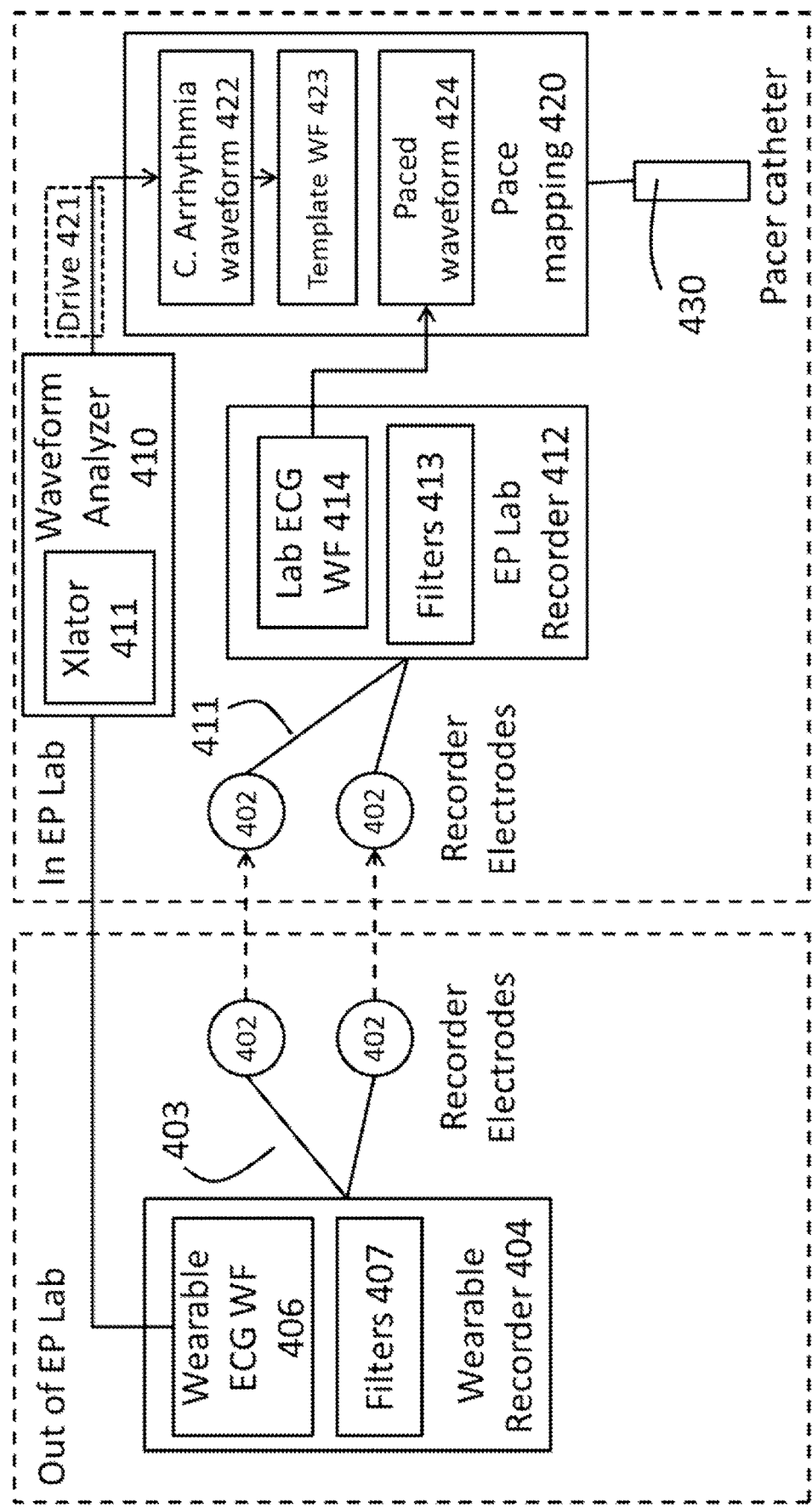
FIGS. 4A-4C are schematic system diagrams and a flow diagram showing a system and method for diagnosis of arrhythmia focus according to some embodiments of the present invention.
Figure 4B:
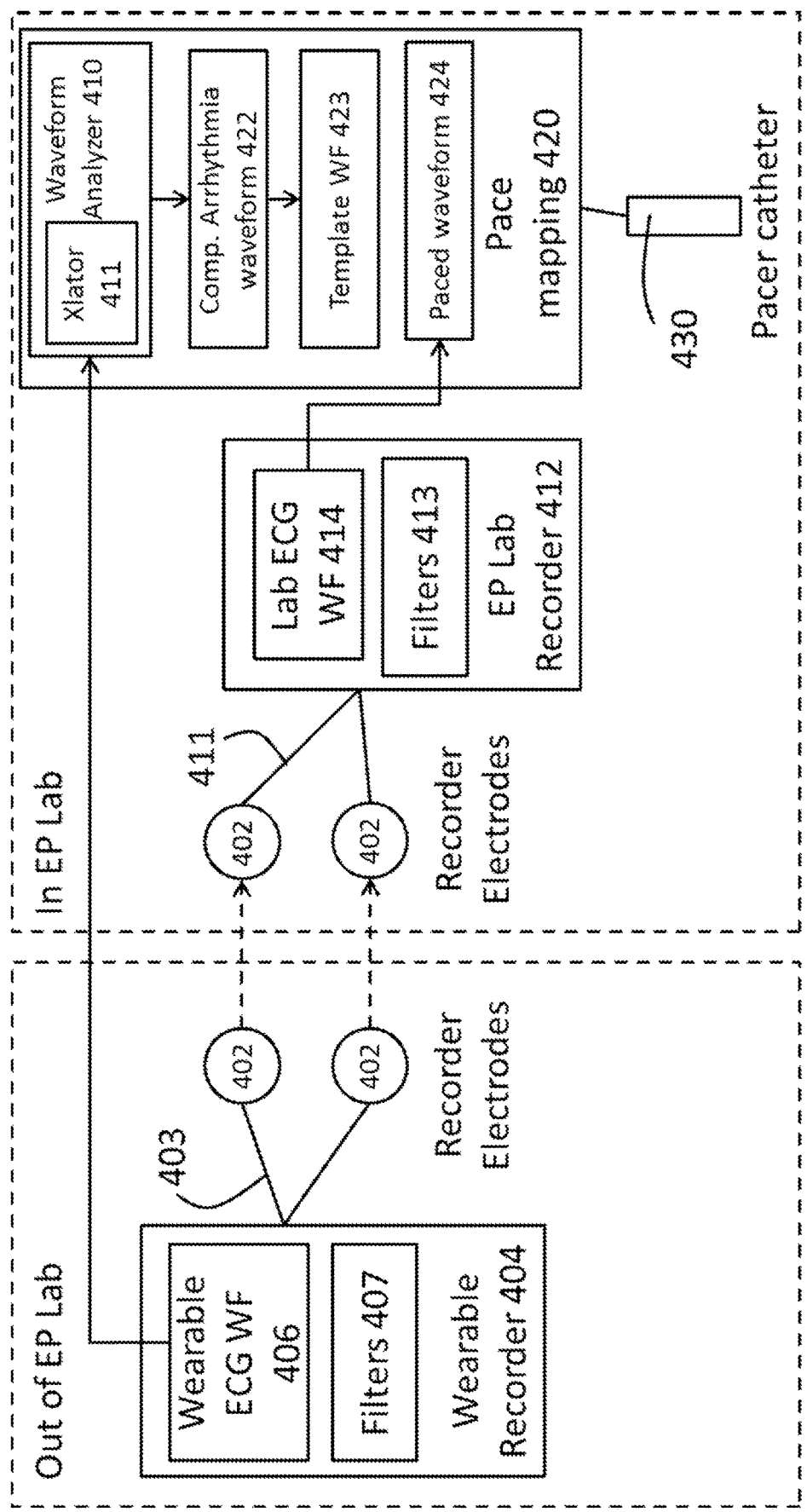
Figure 4C:
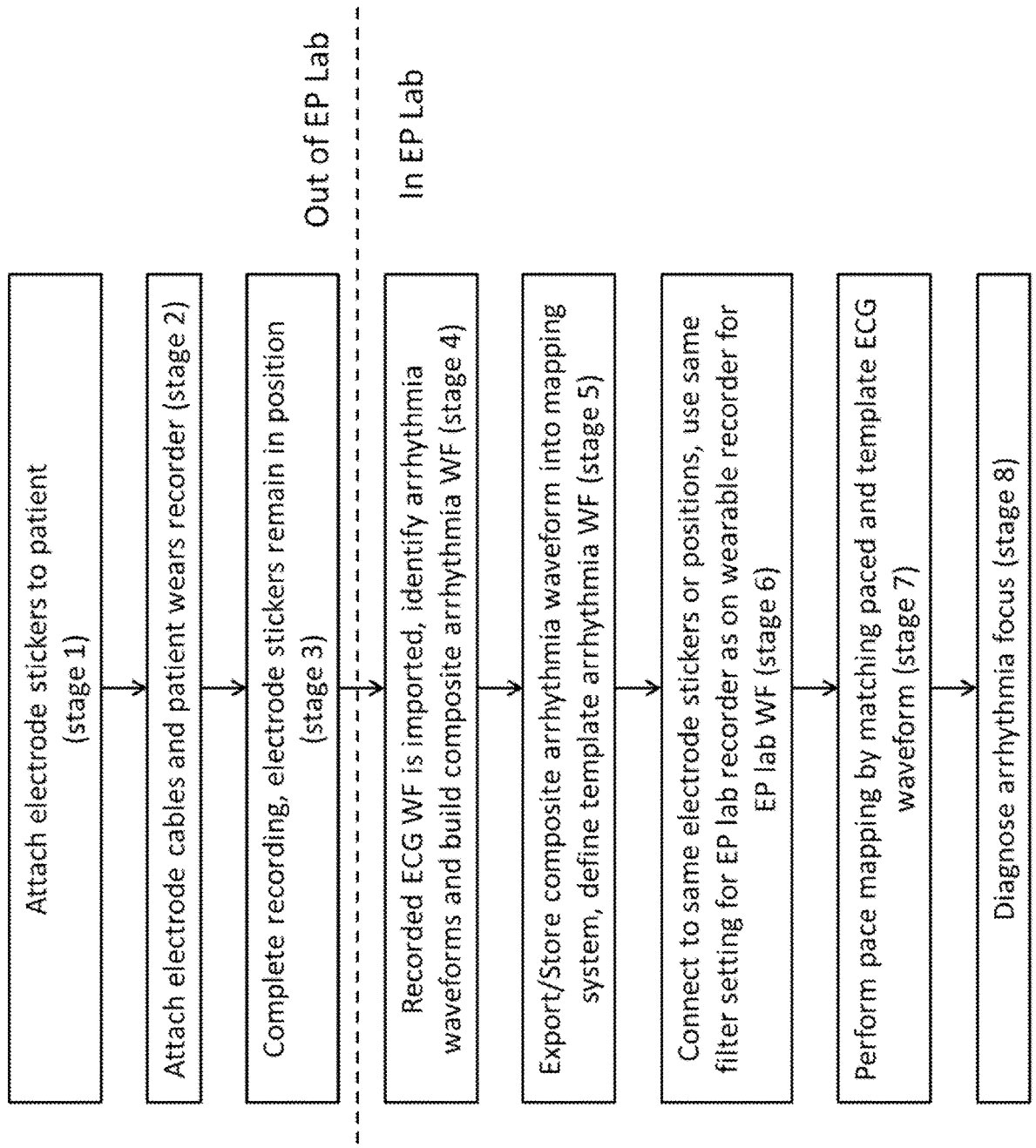

Reference is now made to FIGS. 4A-4C, which are schematic system diagrams and a flow diagram showing a system and method for diagnosis of arrhythmia focus according to some embodiments of the present invention.

As in FIG. 4C, in stage 1 electrode stickers 402 are affixed to a patient. Most preferably ten stickers 402 are affixed to the patient. The sticker placement is as known in the art for 12-lead ECG recording. In stage 2, twelve electrode cables 403 are connected to the stickers 402. Electrode cables 403 are connected to a wearable recorder 404 worn by the patient. Wearable recorder 404 is adapted for 12-lead ECG recording. Recorder 404 then records heart activity as an ECG waveform 406 for an extended period of time typically varying between 24 hours and 72 hours as known in the art. During this time the patient is outside the EP lab and goes about daily activities.

The output of recorder 404 is herein referred to as wearable ECG waveform (WF) 406. ECG WF 406 preferably comprises 12 channels. Optionally, any number of channels may be recorded that provides sufficient data for arrhythmia diagnosis as described herein. ECG WF 406 is stored in recorder 404 on a recording medium. A non-limiting example of a recording medium is flash memory, but other forms of storage may be used. Non-limiting examples of ECG storage formats include SCP-ECG, DICOM-ECG, and HL7 aECG, but other formats may be used. Recorder 404 uses filters 407 to enhance the signal received from electrode stickers 402 and cables 403. Non limiting examples of filters 407 include low pass, high pass, band pass, and notch filters or a combination of these. Filters 407 are configurable and comprise settings that can be duplicated in the same filters used in other ECG recorders.

In stage 3, once sufficient ECG waveform data has been gathered or after completion of the monitoring period, electrode stickers 402 remain affixed to the patient and electrode cables 403 are disconnected from stickers 402 and the recorder 404 is returned to the EP lab for analysis. Analysis may be optionally be performed in a clinic or lab associated with EP lab. Alternatively, stickers 402 are removed and their exact positioning on the patient is marked, such as with a non-limiting example of a marker pen. Alternatively and preferably stickers 402 are provided with a dye or ink which marks the skin of the patient when sticker 402 is applied or removed such that a mark indicating the position of sticker 402 is left on the patient from the dye after sticker 402 is removed.

In stage 4, ECG waveform 406 is imported from recorder 404 into waveform analyzer 410. The importing of ECG WF 406 is performed by wired or wireless connection of recorder 404 to analyzer 410 followed by interaction by an operator with analyzer 410 to initiate the importing. Alternatively the storage media is extracted from recorder 404 and inserted into a storage media reader connected wired or wirelessly to analyzer 410. Alternatively, the importing comprises exporting from the recorder 404 by interaction with the recorder 404. Analyzer 410 is adapted to process the ECG WF 406 in the ECG storage format used by recorder 404.

Alternatively, recorder 404 stores ECG WF 406 in an ECG storage format that can be processed by analyzer 410. Alternatively, analyzer 410 translates the ECG WF 406 ECG format provided by recorder 404 into a format that it can process using a translation module 411 (shown in FIG. 4A as xlator 411). Processing includes manipulation and analysis as described below.

In the embodiment of FIG. 4A, waveform analyzer 410 runs on a standalone computer. Alternatively, in the embodiment of FIG. 4B, analyzer 410 is a software module running on the same computational hardware as pace mapping system 420 described below.

Analyzer 410 preferably comprises a screen (not shown) and interaction means such as a keyboard and mouse (not shown) for viewing and manipulating wearable ECG waveform 406.

ECG waveform 406 is then analyzed to detect arrhythmia waveform patterns. The operator/practitioner now interacts with analyzer 410 to identify waveforms indicating arrhythmia. The arrhythmia waveform portions (such as 422-A and 422-B) are preferably automatically identified by arrhythmia waveform detection software. Alternatively arrhythmia waveform portions are identified by waveform detection software and the identified waveform portions are confirmed by the operator of analyzer 410. Alternatively the operator of analyzer 410 identifies arrhythmia waveform portions. Preferably arrhythmia waveform portions are identified using a combination of the above. Preferably the patient has indicated arrhythmia episodes while wearing Wearable Recorder 404 and operator or software use these indications to locate arrhythmia waveform portions using analyzer 410.

Arrhythmia waveform portions are indicated by operator or software on analyzer 410 based on the start and stop times of the waveform of interest on the recorded timeline. FIG. 4D shows a non-limiting exemplary wearable WF 406 as viewed in analyzer 410. Arrhythmia waveforms 422-A and 422-B have been indicated by operator or software in analyzer 410. Although two portions (422-A and 422-B) are described herein, this is for the sake of simplicity and preferably any number of arrhythmia waveform portions may be indicated and extracted from waveform 406. Therefore at the end of stage 4, arrhythmia waveform portions will have been identified.

Figure 4E:
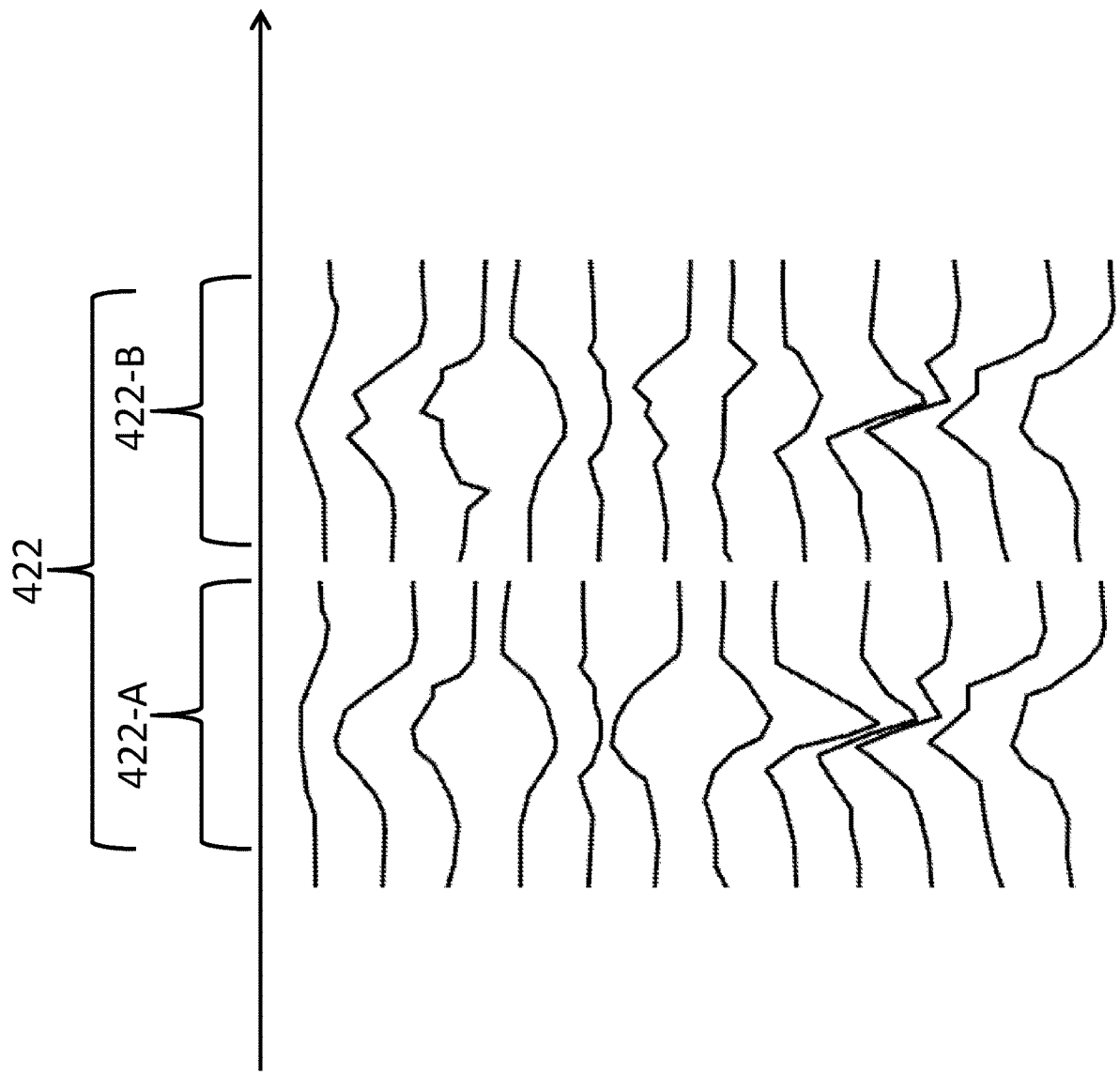

In stage 5, for the embodiment of FIG. 4A, the arrhythmia waveforms 422 are exported from analyzer 410. The waveforms portions, as indicated by the timestamp data from stage 4, are each extracted and then preferably concatenated together to form a composite arrhythmia waveform 422. FIG. 4E shows an exemplary, non-limiting composite arrhythmia waveform 422 comprising indicated waveforms 422-A and 422-B which were extracted from ECG WF 406.

Composite arrhythmia waveform 422 is now exported from analyzer 410 and imported using wired or wireless means into pace mapping system 420. Preferably waveform 422 is exported from analyzer 410 onto removable storage media 421 such as but not limited to a USB storage drive. Preferably drive 421 is adapted for one-time usage to prevent mixing up of patient arrhythmia waveforms 422. Preferably drive 421 comprises encryption mechanisms to prevent patient data stored on drive 421 from being read by systems aside from analyzer 410 and pace mapping system 420. Drive 421 is then connected to mapping system 420 for importing of arrhythmia WF 422 into system 420.

Optionally wearable ECG 406 is in a digital format. Optionally wearable ECG 406 is in an analog format. Optionally composite arrhythmia waveforms 422 are in analog format. Optionally composite arrhythmia waveforms 422 are in digital format. Where wearable WF 406 and composite WF 422 are in different formats (analog or digital), analyzer 410 converts between these formats.

The format of arrhythmia WF 422 is preferably adapted to suit the mapping system 420 used. Optionally, analyzer 410 connects to system 420 via the ECG input port (not shown) of system 420 and mimics the signal that an ECG device would provide to "play back" WF 422 such that system 420 imports, stores and displays constructed arrhythmia waveform 422. Optionally drive 421 is plugged into ECG input port (not shown) of system 420 and mimics the signal that an ECG device would provide to "play back" WF 422 such that system 420 imports, stores and displays constructed arrhythmia waveform 422. Alternatively drive 421 or analyzer 410 are plugged into a data input port (not shown) of system 420 such that system 420 imports, stores and displays constructed arrhythmia waveform 422.

Alternatively, waveform 422 may be saved and exported by analyzer 410 as any standard image file type not limited to jpeg, BMP, PNG, or similar for use by system 420.

Alternatively, as in the embodiment of FIG. 4B where analyzer 410 is a software module of system 420, the arrhythmia waveform 422 is stored in the internal storage of system 420 for use during the pace mapping. Alternatively, arrhythmia WF 422 is stored in a separate file store (not shown).

In the final part of stage 5, arrhythmia WF 422 is analyzed using pace mapping system 420 to create a template waveform 423 for comparison to Lab ECG WF 414.

In stage 6 the patient will return to the EP lab for diagnosis (mapping) of the arrhythmia focus within the heart. Electrode stickers 402 are still affixed to the patient from stage 1. Alternatively, new stickers 402 are affixed at exactly the previously marked positions. In stage 6 electrode stickers 402 are connected to electrode cables 411 of EP lab recorder 412. EP Lab recorder 412 refers to an ECG recorder preferably for 12 channel recording. EP lab recorder 412 comprises filters 413 which are the same as filters 407 and are configured with the same filter settings that were used by filters 407 on wearable recorder 404 for recording wearable ECG WF 406. Optionally, translation module 411 also comprises a filter adaptor module (not shown) for adjusting the ECG WF 406 to match lab ECG WF 414 based on the filters 413 used in EP lab recorder 412. Optionally, wearable recorder 404 is used as EP lab recorder 412, and electrodes 402 optionally remain connected to recorder 404 or are reconnected in the EP lab.

EP lab recorder 412 produces EP lab ECG waveform 414. ECG waveform 414 is provided to pace mapping system 420. System 420 comprises a visual display (not shown) for viewing the lab ECG waveform 414 of recorder 412. The use of the same sticker positions, number of leads, channels and filters ensures that wearable ECG WF 406 and lab ECG WF 414 are compatible and that template waveform 423 extracted from arrhythmia WF 422 can be used as a basis for comparison with paced waveform 424 as described below.

In stage 7, pacing is now performed by probing areas of the heart with pacer catheter 430. ECG waveform 414 is now used by system 420 to provide and display paced waveform 424 which changes as pacer catheter 430 is moved to different positions in the heart. Paced waveform 424 is compared to the template WF 423 derived from arrhythmia waveform 422 until the waveforms sufficiently match and arrhythmia focus is diagnosed at stage 8. Preferably, the comparison is performed by system 420 which provides a numeric percentage match indication on a screen (not shown), such that the medical practitioner can determine the arrhythmia focus based on a high percentage match indication, preferably above 95%. Preferably comparison comprises display of the template and paced waveforms overlapped on the screen (not shown) as illustrated in FIGS. 3B and 3C. Following diagnosis, curative therapy by ablation or other means known in the art may then be performed.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A method for diagnosing arrhythmia focus in the heart of a patient comprising:
   a. affixing a plurality of electrode stickers to a patient;
   b. monitoring the patient by a wearable monitor connected to the plurality of electrode stickers to produce a wearable ECG waveform;
   c. disconnecting said wearable monitor from said plurality of electrode stickers while performing at least one of:
      i. leaving said plurality of electrode stickers affixed to the patient; or
      ii. marking the positions of said plurality of electrode stickers before removing said stickers;
   d. by an analyzer running on a computer, deriving an arrhythmia template waveform or a composite arrhythmia waveform from said wearable ECG waveform and exporting the arrhythmia template waveform or composite arrhythmia waveform into a pace mapping system;
   e. providing an electrophysiology (EP) lab ECG recorder and performing at least one of:
      i. connecting said plurality of stickers to said EP lab ECG recorder; or
      ii. connecting a second set of stickers to said EP lab ECG recorder wherein said second set of stickers are positioned on the marked positions of the plurality of stickers;
   f. pacing the heart of the patient using a pacing electrode; and
   g. in the pace mapping system, comparing the paced ECG waveform provided by said EP lab ECG recorder with the provided arrhythmia template waveform or composite arrhythmia waveform to diagnose the arrhythmia focus.

2. The method of claim 1 wherein said wearable ECG waveform comprises up to twelve channels.

3. The method of claim 2 wherein said wearable monitor filters the signal received from said plurality of electrode stickers using one or more wearable monitor filters.

4. The method of claim 3 wherein said pace mapping system and said analyzer run on the same computer.

5. The method of claim 3 wherein said EP lab recorder comprises one or more EP lab recorder filters and wherein said EP lab recorder filters are the same as the wearable monitor filters and are configured with the same filter settings.

6. The method of claim 1 wherein the exporting includes transferring the arrhythmia template waveform or composite arrhythmia waveform from the analyzer to a storage device and connecting said storage device to said pace mapping system for importing said arrhythmia template waveform or composite waveform from said storage device into said pace mapping system.

7. The method of claim 1 wherein the exporting is selected from the group consisting of:
  a. adapting said arrhythmia template waveform or composite waveform to a file format that can be used by said pace mapping system and importing said file into said pace mapping system;
  b. connecting said analyzer to said pace mapping system via the ECG input port of said pace mapping system and mimicking by said analyzer the signal that the EP lab ECG recorder would provide to said port;
  c. adapting said arrhythmia template waveform or composite waveform to an image file format that can be used by said pace mapping system and importing said file into said pace mapping system; and
  d. a combination of the above.

8. The method of claim 1, wherein comparing the paced ECG waveform with the composite arrhythmia waveform comprises deriving an arrhythmia template waveform from the composite arrhythmia waveform and comparing the paced ECG waveform with the arrhythmia template waveform.

* * * * *